United States Patent
Kinast

(10) Patent No.: US 9,149,228 B2
(45) Date of Patent: Oct. 6, 2015

(54) PATIENT-WORN MEDICAL MONITORING DEVICE

(71) Applicant: Eric Kinast, Santa Ana, CA (US)

(72) Inventor: Eric Kinast, Santa Ana, CA (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 0 days.

(21) Appl. No.: 14/201,669

(22) Filed: Mar. 7, 2014

(65) Prior Publication Data

US 2014/0221766 A1    Aug. 7, 2014

Related U.S. Application Data

(60) Division of application No. 11/642,356, filed on Dec. 20, 2006, now Pat. No. 8,668,643, which is a continuation of application No. 10/341,833, filed on Jan. 14, 2003, now Pat. No. 7,257,438, which is a continuation-in-part of application No. 10/201,075, filed on Jul. 23, 2002, now abandoned.

(60) Provisional application No. 60/308,070, filed on Jul. 26, 2001.

(51) Int. Cl.
*A61B 5/00* (2006.01)
*A61B 5/0404* (2006.01)
*A61B 5/11* (2006.01)
*A61B 5/0245* (2006.01)

(52) U.S. Cl.
CPC .............. *A61B 5/6832* (2013.01); *A61B 5/0002* (2013.01); *A61B 5/0031* (2013.01); *A61B 5/0404* (2013.01); *A61B 5/1116* (2013.01); *A61B 5/6822* (2013.01); *A61B 5/6831* (2013.01); *A61B 5/6833* (2013.01); *A61B 5/6841* (2013.01); *A61B 5/72* (2013.01); *A61B 5/0245* (2013.01); *A61B 2560/04* (2013.01); *A61B 2560/0468* (2013.01); *A61B 2562/08* (2013.01); *A61B 2562/227* (2013.01)

(58) Field of Classification Search
None
See application file for complete search history.

(56) References Cited

U.S. PATENT DOCUMENTS

| | | |
|---|---|---|
| 3,943,918 A | 3/1976 | Lewis |
| 4,275,385 A | 6/1981 | White |
| 4,635,646 A | 1/1987 | Gilles et al. |
| 4,662,378 A | 5/1987 | Thomis |
| 4,958,645 A | 9/1990 | Cadell et al. |
| 4,981,141 A | 1/1991 | Segalowitz |
| 5,027,824 A | 7/1991 | Dougherty et al. |
| 5,153,584 A | 10/1992 | Engira |

(Continued)

OTHER PUBLICATIONS

USPTO, Office Action for U.S. Appl. No. 11/642,356 mailed Aug. 21, 2013.

(Continued)

*Primary Examiner* — Brian T Gedeon
(74) *Attorney, Agent, or Firm* — Kory D. Christensen; Stoel Rives LLP

(57) ABSTRACT

One embodiment of a medical monitor includes a lanyard and an electronic package supported in the manner of a pendant. Another embodiment of a medical monitor attaches adhesively to a patient. Both embodiments include a reusable portion housing electronic components for processing measurements of the patient's physiological condition, and a disposable portion including a battery. The physiological measurements may be transmitted to a remote location along with a signal identifying the patient.

9 Claims, 10 Drawing Sheets

(56) References Cited

U.S. PATENT DOCUMENTS

| | | | |
|---|---|---|---|
| 5,396,224 | A | 3/1995 | Dukes et al. |
| 5,458,123 | A | 10/1995 | Unger |
| 5,942,986 | A | 8/1999 | Shabot et al. |
| 5,944,659 | A | 8/1999 | Flach et al. |
| 6,049,730 | A | 4/2000 | Kristbjarnarson |
| 6,215,403 | B1 | 4/2001 | Chan et al. |
| 6,454,708 | B1 * | 9/2002 | Ferguson et al. .............. 600/300 |
| 6,970,097 | B2 | 11/2005 | Welles et al. |
| 7,840,275 | B2 | 11/2010 | Verhoef |
| 7,889,069 | B2 | 2/2011 | Fifolt et al. |
| 2003/0004403 | A1 | 1/2003 | Drinan et al. |
| 2004/0077937 | A1 | 4/2004 | Yarden |
| 2014/0051946 | A1 * | 2/2014 | Arne et al. .................... 600/301 |

OTHER PUBLICATIONS

USPTO, Office Action for U.S. Appl. No. 11/642,356 mailed Dec. 6, 2010.

USPTO, Office Action for U.S. Appl. No. 11/642,356 mailed Apr. 18, 2013.

USPTO, Office Action for U.S. Appl. No. 11/642,356 mailed Mar. 11, 2010.

USPTO, Office Action for U.S. Appl. No. 11/642,356 mailed Jul. 8, 2009.

USPTO, Office Action for U.S. Appl. No. 10/341,833 mailed May 25, 2006.

USPTO, Office Action for U.S. Appl. No. 10/341,833 mailed Sep. 29, 2005.

* cited by examiner

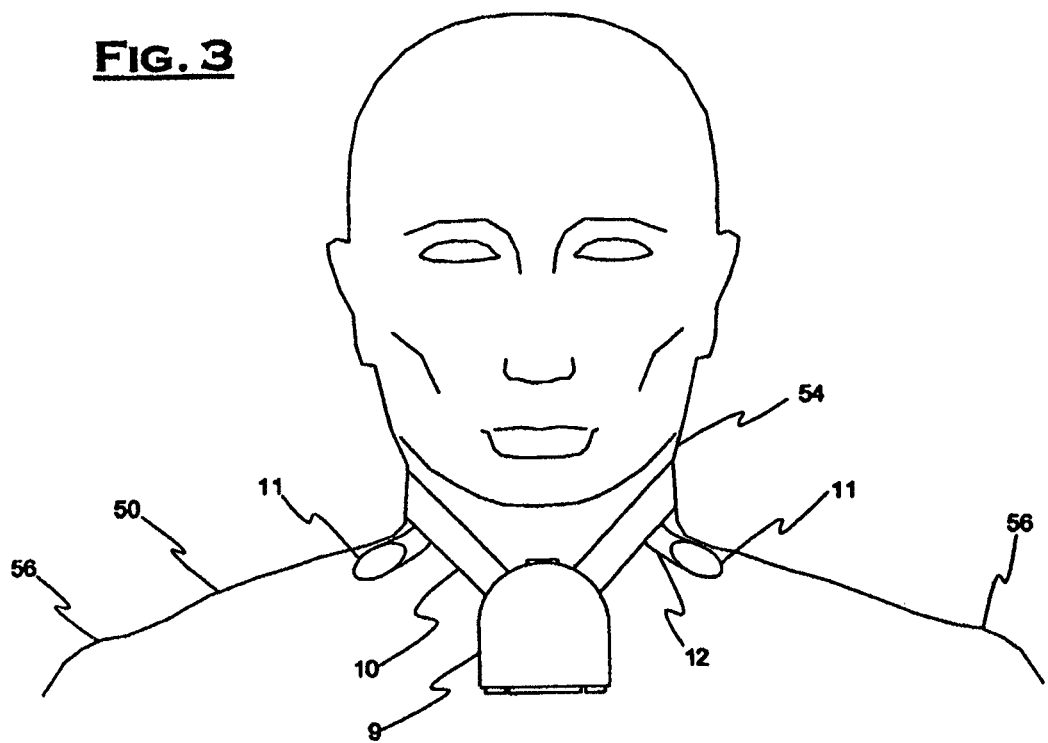

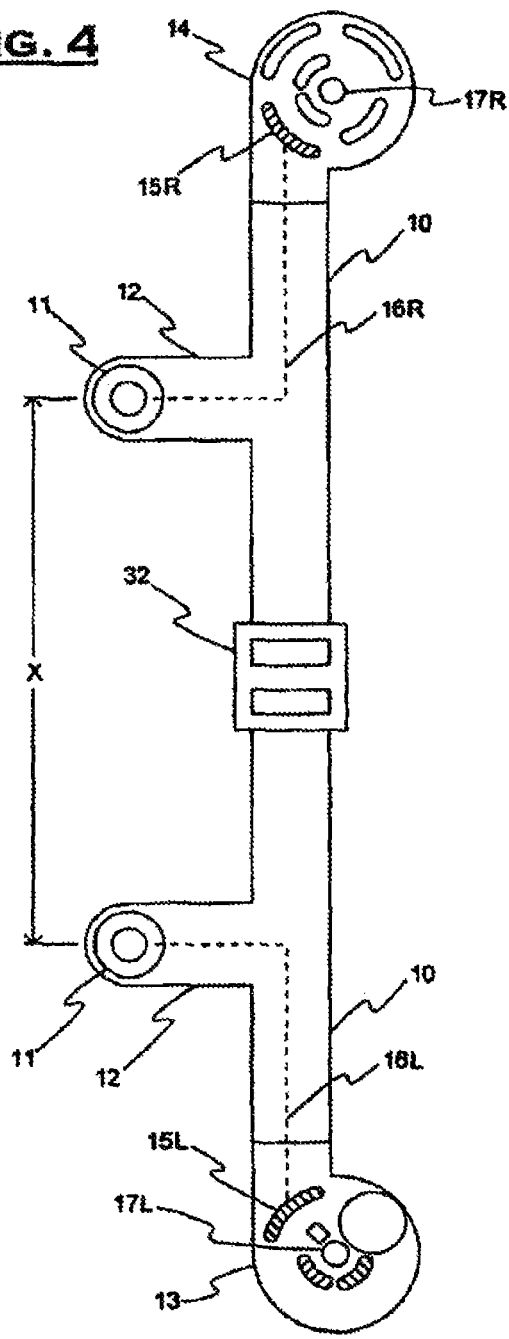

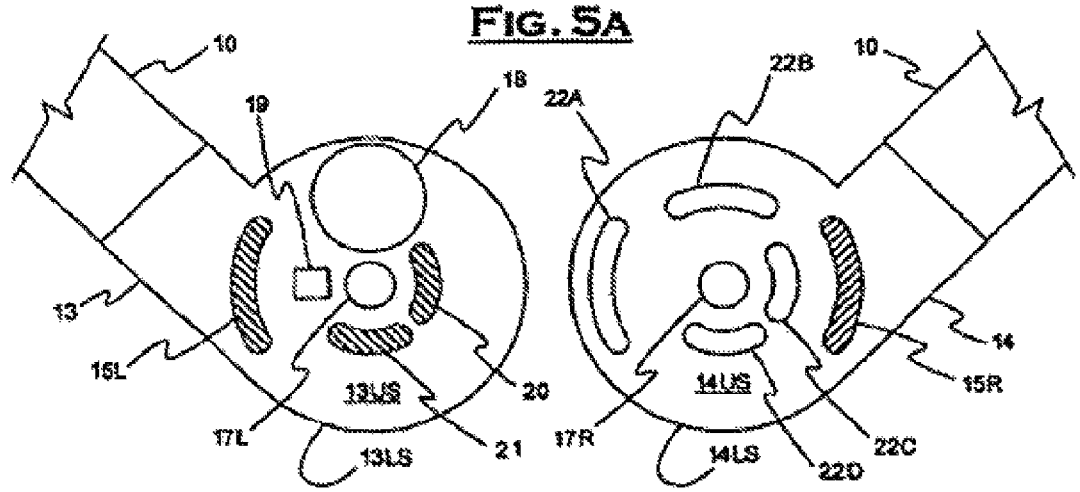
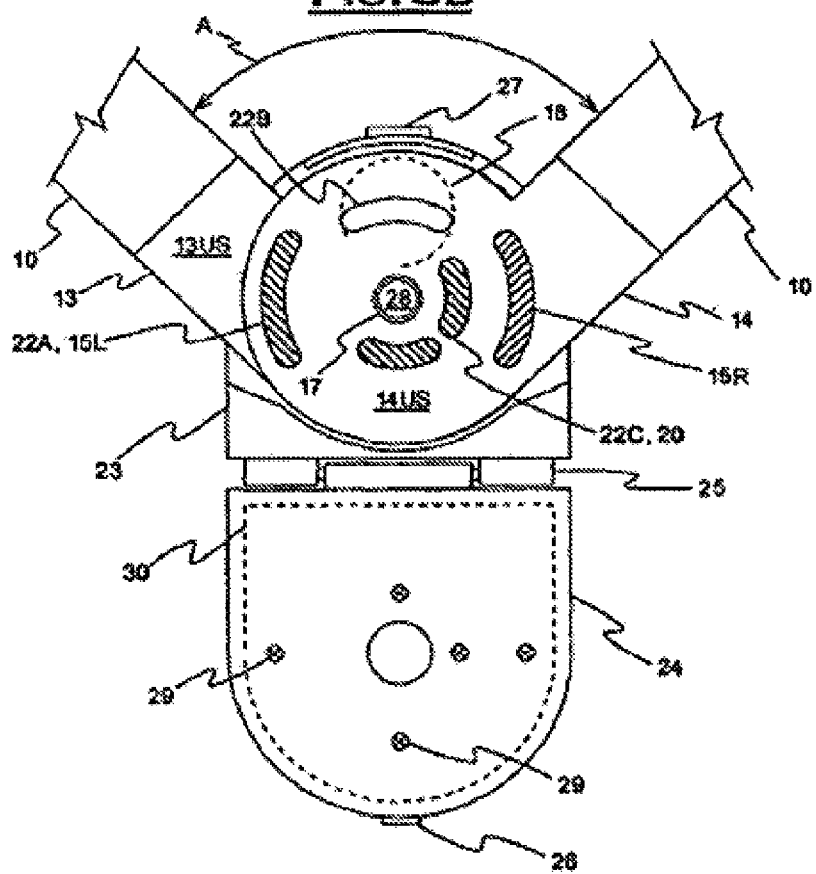

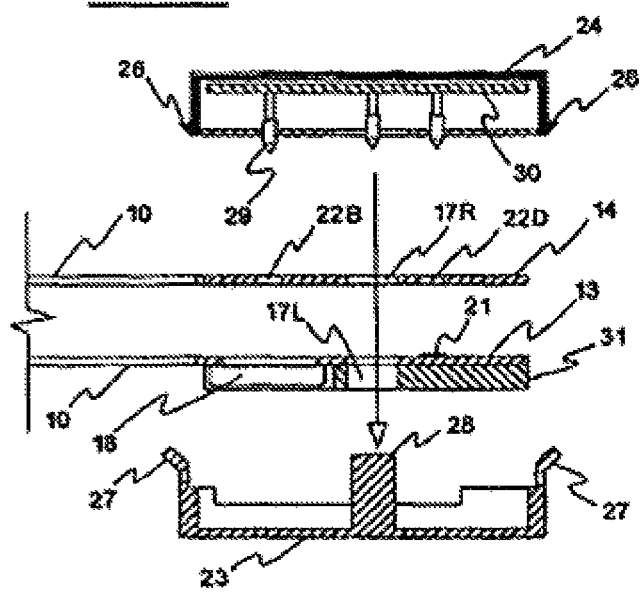
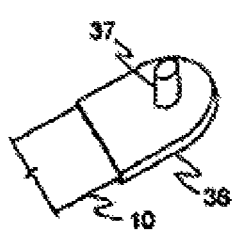 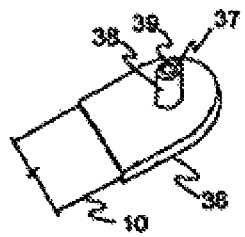 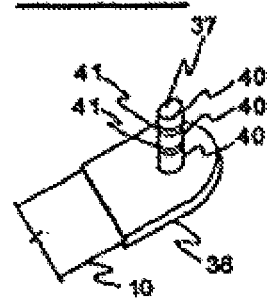

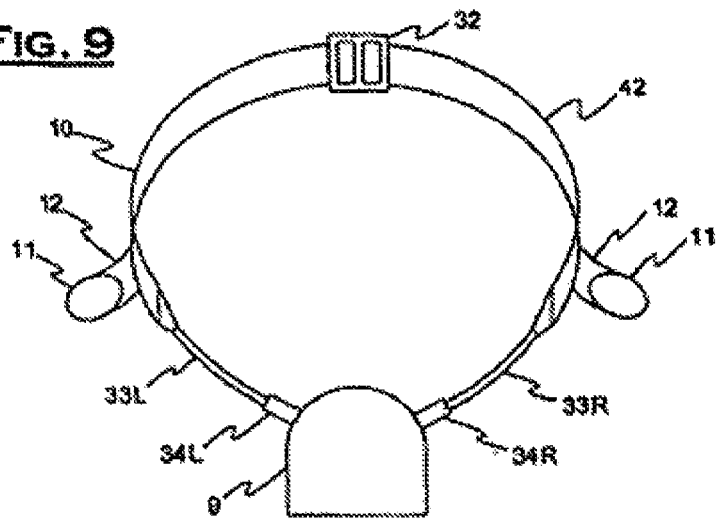
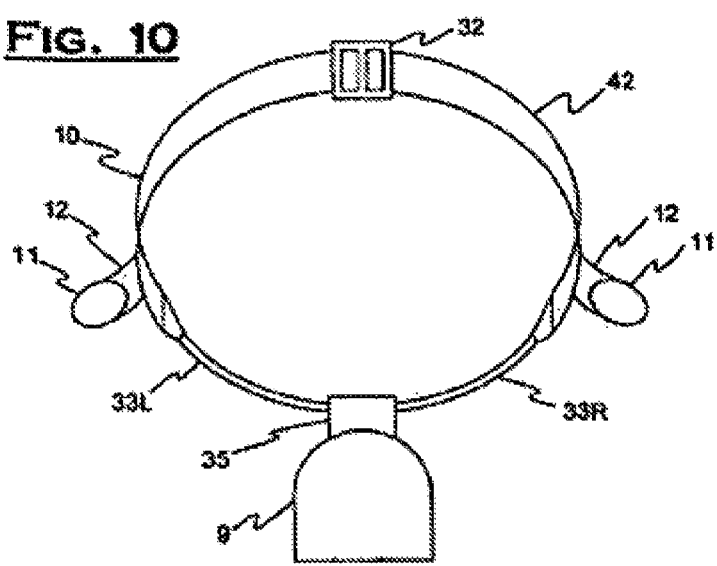

PATIENT-WORN MEDICAL MONITORING DEVICE

CROSS-REFERENCE TO RELATED APPLICATIONS

This application is a continuation of U.S. patent application Ser. No. 10/341,833, filed on Jan. 14, 2003, which is a continuation-in-part of U.S. patent application Ser. No. 10/201,075, filed on Jul. 23, 2002, the disclosures of which are hereby incorporated by reference herein, and claims the benefit of the filing date of Provisional Application No. 60/308,070, filed on Jul. 26, 2001.

BACKGROUND OF THE INVENTION

1. Field of the Invention

The invention relates to a medical monitoring device. More particularly, the invention relates to a device for monitoring the condition and location of a subject or patient.

2. Description of the Prior Art

Modern medical practice makes extensive use of electronic vital signs monitoring. As technology has progressed, electronic monitoring devices have become more compact, easier to use, and have been made available to larger segments of the patient population. Today, most electronic monitors are what are termed "bedside monitors."

A bedside monitor consists of an electronics and display unit placed in close proximity to a patient bed. Cables connect the monitor to various sensors attached to the patient. While such arrangements have become highly developed, and permit comprehensive monitoring of the patient, the disadvantages are obvious. A patient can only be monitored when confined to bed, or otherwise restricted to the immediate vicinity of the monitor, as dictated by the connecting cables.

Portable or transportable monitors have been developed to allow the patient to be moved within the hospital, or even between healthcare facilities. Such monitors are quite similar to traditional bedside monitors, but are made somewhat smaller and lighter in weight, and have provision to operate for some time from internal battery power. But such devices remain sufficiently heavy and bulky that they require special attention to move along with the patient. Often, the monitor is provided with a bracket or other arrangement allowing it to be attached to the wheeled bed occupied by the patient during transport. While such an arrangement makes it possible to relocate a patient while continuing monitoring, it does not permit normal ambulation of the patient.

In many cases, patients are sufficiently able-bodied that they may ambulate normally, and are not confined to bed, yet it is desired to continuously monitor their condition. Indeed, in some cases ambulation of the patient is a necessary part of medical care, as in the case of a heart patient where the exertion associated with walking and other normal activity may be necessary to reveal an underlying heart condition. To serve these cases, patient-worn monitoring devices have been developed. Often, such devices are limited to monitoring a single vital sign. As the heart may be considered the most vital organ, the usual parameter to be monitored is the electrocardiogram, or ECG.

Patient-wearable devices used to monitor a patient's ECG take two general forms. One form of device, often known as a holter monitor, simply records the patient's ECG signal for later analysis. The particular advantage of this sort of device is that monitoring can take place at any location, while the patient is going about normal daily activities. However, an obvious disadvantage is that there is no immediate indication of a deterioration in the patient's condition. Therefore, an alternate device, known as a telemetry monitor, has been developed. Such a device acquires the patient's ECG signal, and transmits it by radio link to a central monitoring and display location, where the ECG signal can be observed by clinical personnel and automated analysis systems. Any change in the patient's condition requiring clinical intervention is therefore immediately apparent and medical assistance can be dispatched to the patient. The disadvantage of telemetry systems is that they are operable only within premises where suitable receiving equipment is provided.

Current ambulatory ECG monitors found in clinical applications use electrodes of a type and configuration based on bedside monitor practice. Generally, three to five adhesive electrodes are attached to the body in locations disposed on the chest. These electrodes are connected by leadwires or a cable to the monitor electronics. The monitor electronics is arranged in a wearable housing, generally supported by means of a pouch, sling, or belt clip. This arrangement is somewhat inconvenient, due to the presence of the leadwires and the bulk, weight, and method of support of the monitor electronics. Further, some skill is necessary to properly attach the electrodes, connect the leadwires and set the monitor in action. As such, monitoring devices of this type are only used in such clinical cases where the inconvenience and cost of the skilled application are justified.

Electrocardiogram devices using conventional electrode configurations can yield considerable information about the condition of the heart by skilled interpretation of the ECG waveforms produced. However, in many cases, even in clinical practice, such interpretation is not performed, and the monitor is used only to measure the patient's heart rate. This is always the case in certain non-clinical ECG applications, such as when the ECG signal is used to determine the pulse rate during exercise. In this case, conventional placement of electrodes can be abandoned in favor of electrode configurations which facilitate convenient application of the monitoring device. Exercise ECG monitors are often configured as a small electronics housing secured by a belt tightened around the wearer's chest. The housing contains a pair of electrodes which contact the chest and acquire an ECG signal. The electronics trigger on each heartbeat and transmit a signal to a nearby readout device. The readout device counts the trigger signals within a unit time and displays the pulse rate.

While such exercise monitors are far simpler to apply and lack the objectionable leadwires and separate electronics box of clinical ambulatory monitors, they do not answer fully to clinical purposes, even where it is only desired to measure the heart rate. The electronics, signal processing and signal transmission used by these devices are not well adapted to clinical requirements. These defects, however, can be remedied by modification of the electronics in well-known ways. Of greater importance is the fact that the encircling belt is not well adapted to long term wear. In order to secure the device against accidental displacement, the belt must be tightened to a degree that proves objectionable over an extended period. If the belt is loosened one runs the risk of a temporary loss of electrode contact during exercise or while the patient is laying or shifting in bed. Further, the electrodes used in commercial exercise monitors often depend on some degree of perspiration to reduce the electrical resistance of the electrode contact. While perspiration is inevitably present in exercise sufficiently strenuous to merit pulse rate monitoring, its presence cannot be assumed in the clinical setting. Finally, even if tension and electrode issues were resolved, the position of the device across the chest is not optimal for patient and clinician convenience. Application of the device to this region can in some cases constitute an insult to patient dignity. More importantly, the position of the belt may interfere with the application of defibrillator electrodes, the placement of a stethoscope, or other common medical procedures.

It is desirable to expand clinical electronic monitoring to a greater population of patients. This is only practical if an arrangement less unwieldy than traditional clinical ambulatory monitors is adopted. While commercial exercise monitors considerably simplify the monitoring arrangement, they still do not answer well to the needs of such expanded clinical monitoring.

Patient-worn devices also exist which give an indication of the location of the patient. A typical prior art system is described in U.S. Pat. No. 4,958,645 entitled Multi-Channel Digital Medical Telemetry System, which issued on Sep. 25, 1990 to Cadell et al. The medical radio telemetry system described therein utilizes a plurality of antennas which are distributed throughout a hospital or other premises. The patient is outfitted with a radio receiver and transmitter to collect a patient physiological signal, including, for example, the patient's temperature, heart rate, pacer rate, respiration rate, brain activity level, and blood pressure level. The transmitter and receiver associated with the patient operate in conjunction with one or more room locator transmitters spaced in rooms where the patient is being monitored. The room locator transmitters emit signals indicative of the room they are emanating from. Signals from the room locator transmitters are combined with the patient signals so as to enable hospital staff to monitor the location of the patient.

U.S. Pat. No. 4,981,141, entitled Wireless Electrocardiographic Monitoring System, issued on Jan. 1, 1991 to Segalowitz, discloses an electrocardiographic monitoring system where the patient's heart-signaling sensing electrodes are each coupled to the heart-signal monitor/recorder by wireless transmitters and corresponding wireless receivers in a base unit. Each transmitter/receiver combination operates at a separate radio frequency to provide a zero or reference signal at the base unit which is used to modulate a signal transmitter at the base unit. Each modulated signal, when received and demodulated, provides information concerning signals sensed by an electrode carried by the patient, such as, for example, the right-leg electrode, etc.

It is clear from the above that it is extremely desirable to monitor various vital signs of an ambulatory patient. This is even more important due to the recent trend to get patients ambulating as soon as possible. It is also important to determine the location of a monitored patient within, for example, the confines of a hospital or other area so as to ensure expedient care, such as in the case of an emergency.

Despite the devices that are currently available for monitoring ambulatory patients, there is a need for improved devices that are light in weight, lower in cost and easy to use.

SUMMARY OF THE INVENTION

Accordingly, it is an object of the invention to produce an arrangement of electrodes or other signal sensors or electronics and a mechanical attachment to the patient for said sensors or electronics, which provide convenience, comfort, dignity and low applied cost.

It is a further object of the invention to integrate the electrodes or sensors, electrical connections thereto, mechanical support for the electronics, and where applicable, a power source, into a single, preferably disposable, component.

It is a still further object of the invention to arrange the electrodes or sensors, electrical connections thereto, mechanical support for the electronics, and where applicable, a power source, so that they can be placed securely on the body of a patient with minimal discomfort and insult to dignity.

One embodiment of the invention is a lanyard hung about the neck, from which the medical monitoring electronics is supported in the manner of a pendant. The lanyard includes integral electrodes or other sensors, auxiliary components and electrical connections thereto.

Another embodiment of the invention is a monitoring device, including a first portion having an electronic circuit; and a disposable portion removably connectable to the first portion, the disposable portion including a power source, whereby power from the power source is supplied to the electronic circuit upon connection of the disposable portion to the first portion.

Yet another embodiment of the present invention is a monitoring device, including a first portion having an electronic circuit; a disposable portion removably connectable to the first portion; and an adhesive support for adhering the disposable portion to a subject.

A still further embodiment of the present invention is a method for monitoring a subject, including providing a monitoring device having at least one sensor operable to detect a physiological condition of the subject and to generate condition data representative of the physiological condition, the monitoring device being operable to communicate wirelessly with a receiver; operatively connecting the monitoring device to the subject with the at least one sensor connected to the body of the subject; processing the condition data in the monitoring device to create processed data; and transmitting the processed data to the receiver.

Yet a further embodiment of the present invention is a method for locating a subject within a defined area, the method including providing a plurality of receivers at spaced locations in the defined area, each receiver having a specified location, a predetermined reception range and receiver identification data identifying the receiver, the reception range of each receiver overlapping with the reception range of at least one next closest receiver; wirelessly transmitting first data from a transmitter connected to the subject, the first data including subject identification data identifying the subject; receiving the first data at at least one of the receivers when the transmitter is within the reception range of the at least one receiver; and transmitting second data from the at least one receiver to a central station, the second data including the subject identification data and the receiver identification data for the at least one receiver, whereby the central station uses the subject identification data and the receiver identification data to locate the subject.

Still a further embodiment of the present invention provides a system for monitoring a plurality of subjects in a defined area, the system including a plurality of monitors, one of the monitors being connected to each subject. Each monitor includes at least one sensor operable to detect a physiological condition of the subject and to generate condition data representative of the physiological condition; a processor operable to process the condition data to create processed data including subject identification data identifying the subject; and a transmitter operable to transmit the processed data wirelessly. The system further includes at least one receiver having a reception range, the at least one receiver being operable to receive the transmitted data from ones of the monitors within the reception range; and a central station operable to receive second data from the at least one receiver, the second data including the subject identification data and receiver identification data identifying the at least one receiver, the central station being further operable to use the subject identification data and the receiver identification data to locate subjects within the reception range of the at least one receiver.

To the accomplishment of the above and related objects, the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are designated by like reference numerals. The drawings are briefly described as follows:

FIG. 3 is a frontal view of a patient wearing the pendant monitor of the present invention around his neck.

FIG. 4 is a plan view of the pendant monitor lanyard of FIG. 3 in a flattened configuration.

FIG. 5A is a plan view of the articulated ends of the lanyard portion of the pendant monitor, which fit into the electronics housing.

FIG. 5B is a plan view of the ends of the lanyard of FIG. 5A in position in the open electronics housing.

FIG. 7 is a longitudinal cross-sectional view of an alternate embodiment of the electronics housing of FIG. 6, not employing a hinge.

FIG. 8A is a perspective view of an alternate embodiment of the articulated lanyard ends including a conductive anchor post.

FIG. 8B is a perspective view of an alternate embodiment of the articulated lanyard ends including a coaxial conductive anchor post.

FIG. 8C is a perspective view of an alternate embodiment of the articulated lanyard ends including a conductive anchor post having three electrical contacts.

FIG. 9 is a perspective view of an alternate embodiment of the lanyard assembly employing flexible cords.

FIG. 10 is a perspective view of an alternate embodiment of the lanyard assembly with a single attachment connector.

DETAILED DESCRIPTION

Figure 1:
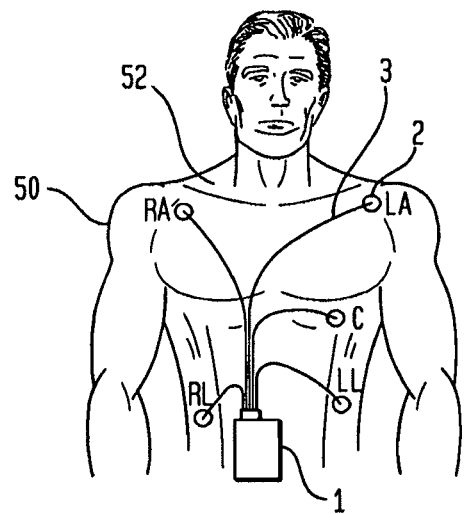
FIG. 1 is a frontal view of a patient connected to a prior art clinical ambulatory monitor.

FIG. 1 illustrates a commonly used prior art clinical ambulatory ECG monitor connected to a chest 52 of a patient 50. Several leadwires 3 extend from a housing 1 to a plurality of electrodes 2 attached to chest 52. Electrodes 2 are labeled RA, LA, RL, C and LL. Housing 1 contains monitoring electronics and is generally supported by a sling (not shown in the figure) or arranged to be clipped to the patient's belt or the waistband of the patient's clothing. This support arrangement is objectionable due to the bulk and weight of the electronics and housing 1 and due to the often encountered difficulty of housing 1 falling loose from its support or attachment.

A rather aggressive adhesive is generally necessary to attach electrodes 2 because they must not only remain securely in contact with chest 52, but must also support the weight and possible tension of leadwires 3. The use of a strong adhesive results in considerable discomfort during removal of electrodes 2 and, in some cases, irritation while they are in place. Further, the numerous leadwires 3 are inconvenient, subject to tangling and may become accidentally detached from electrodes 2. The presence of the wires may also prove disconcerting to patient 50, in that they appear excessively "technical" in nature and may cause patient 50 undue concern over his or her condition.

The electrode arrangements used by the type of prior art monitor illustrated in FIG. 1 are adapted from traditional bedside monitors. A common arrangement is to use five electrodes, as shown in FIG. 1. These are commonly designated RA (right arm), LA (left arm), LL (left leg), RL (right leg), and C (chest), according to the body landmarks near which they are placed. One of the electrodes 2, in this case RL, is designated as a reference electrode. The remaining electrodes 2 are connected to the inputs of several channels of ECG amplifiers. A number of standard ECG vectors, or "leads", can be obtained by taking various combinations of the differential voltages obtained between pairs of electrodes 2. In conventional practice, seven such vectors, commonly designated Lead I, Lead II, Lead III, aVR, aVL, aVF, and C are often used. All seven vectors can be obtained simultaneously, by suitable arrangement of the ECG amplifiers, according to well-known methods.

In a common alternate electrode arrangement, only three electrodes are placed, generally at the locations RA, LA, and LL. In this case, one of the three electrodes is designated the reference electrode, and the ECG amplifier inputs are connected to the remaining two. Although three permutations are possible, giving rise to the ECG vectors Lead I, Lead II, and Lead III, only one vector can ordinarily be obtained at a time in this case.

The use of the reference electrode is necessary in bedside monitor designs, and is somewhat necessary in ambulatory monitors using leadwires, because it greatly facilitates rejection of interference from the AC mains and similar common-mode interference sources. However, if the leadwires are dispensed with, and the monitor electronics and connections are held in intimate proximity to the patient's body, the mechanisms by which common mode interference is injected into the ECG signal are minimized. Under these conditions, operation without a reference electrode becomes more practical.

Figure 2:
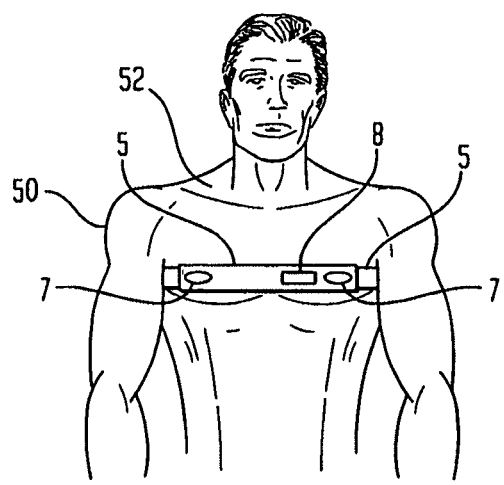
FIG. 2 is a frontal view of a patient wearing a prior art exercise monitor.

The prior art exercise monitor illustrated in FIG. 2 takes advantage of such a two electrode arrangement. Monitor components are contained in a housing 5, which is held in contact with chest 52 of subject 50 by belt 6. The face of housing 5 touching the skin contains two electrodes 7 which contact the skin and acquire an ECG signal. Electronics 8 are also carried within the housing, and connect to electrodes 7 through wires or other conductive path embedded in the housing (not shown). Because electrodes 7, electronics 8, and their interconnections all lie in very close proximity to the patient's body, there is little opportunity for pickup of common mode interference, as from the AC mains. This is because the compact arrangement of the electrodes 7, wiring (not shown), and electronics 8 provides very low coupling capacitance to interference sources, while the close proximity to the body provides much larger capacitance to the body. In effect, the patient's body provides a significant measure of electrostatic shielding. As such, given reasonable electrode impedances, such a configuration can operate successfully without an additional reference electrode, and even with a single-ended, rather than the usual differential, ECG amplifier. Therefore, it is possible to operate with just two ECG electrodes. However, as the electrode locations in this device differ from those used in conventional monitoring practice, the waveform morphology of the ECG signal will differ, and some of the diagnostic value of the waveform will be lost. This is not of concern in cases where it is only desirable to measure the heart rate and rhythm, so long as the waveform obtained clearly shows the important features of the ECG signal, such as the R-wave.

While such exercise monitors are far simpler to apply and lack the objectionable leadwires and separate electronics box of clinical ambulatory monitors, they do not answer fully to clinical purposes, even where it is only desired to measure the heart rate. The electronics, signal processing and signal transmission used by these devices are not well adapted to clinical requirements. These defects, however, can be remedied by modification of the electronics in well-known ways. Of greater importance is the fact that encircling belt 6 is not well adapted to long term wear. In order to secure the device against accidental displacement, belt 6 must be tightened to a degree that proves objectionable over an extended period. If belt 6 is loosened, one runs the risk of a temporary loss of electrode contact during exercise or while the patient is laying or shifting in bed. Further, the electrodes used in commercial exercise monitors often depend on some degree of perspiration to reduce the electrical resistance of the electrode contact. While perspiration is inevitably present in exercise sufficiently strenuous to merit pulse rate monitoring, its presence cannot be assumed in the clinical setting. Finally, even if tension and electrode issues were resolved, the position of the device across the chest is not optimal for patient and clinician convenience. Application of the device to this region can in some cases constitute an insult to patient dignity. More importantly, the position of belt 6 may interfere with the application of defibrillator electrodes, the placement of a stethoscope, or other common medical procedures.

Similar to the prior art monitoring device of FIG. 2, the present invention takes advantage of a two electrode system. At the same time, however, the present invention overcomes the above described drawbacks by providing for a pendant monitor that takes advantage of support provided by the shoulder and neck region of the body, which provides a useful monitoring location. The shoulder and neck region is convenient to access without loss of patient dignity. Furthermore, the neck provides a natural means for supporting the weight of a monitor device attached to the electrodes. Electrodes and electronics located in this area are unlikely to be an encumbrance to the patient or disrupt most clinical procedures.

The heart's electrical activity can be modeled as an electric dipole which varies both in orientation and amplitude over the cardiac cycle. Such a dipole introduces electric field lines connecting its endpoints in the surrounding media. It is these field lines that give rise to the potentials observed at surface electrodes. The potential developed is dependent on the strength of the field, the separation of the electrodes and the angle between the axis of the electrodes and the field lines. The potential is ideally greatest when the field is parallel to the electrode axis and zero when orthogonal. It is for this reason that different electrode orientations produce differing ECG waveform morphologies, since the relative orientations of the electrode axis and the electric field corresponding to a particular feature of the waveform will dictate the amplitude and polarity with which that feature appears on the waveform. Conventional ECG electrode placements have been selected with the intention of providing useful and informative "views" of the heart's electrical activity during the various phases of the cardiac cycle. Note that, according to well-known principles of field mapping, the electric field lines permeate the medium surrounding the dipole causing them. Therefore, although the strongest signals may be obtained with electrodes located near the ends of the dipole, weaker signals are obtained at other locations, including even when the dipole does not lie between the electrodes. There are, of course, cases when no signal is obtained, such as in the case of orthogonality, or when some distortion of the field prevents the field lines from reaching the electrode site.

The body has non-uniform electrical conductivity and is not infinite in extent. Therefore, the actual body surface potentials are considerably distorted from those that would ideally exist were the heart's electric dipole to induce its electric field lines in a homogenous, infinite medium. Nevertheless, the above generalizations still generally apply. As such, it is possible to obtain ECG signals of diminished amplitude from electrodes located elsewhere than surrounding the heart on the chest. Such locations, however, are preferably on the trunk of the body, as few field lines fringe into narrow extremities. Hence, little signal will be obtained between two electrodes placed on one arm, as few field lines pass into the extremity. On the other hand, a large signal is obtained from one arm to the other, because in this case the arms serve as conductive pathways between opposite sides of the torso, where a strong field exists.

For these reasons, a useful ECG signal can be obtained at the top of the shoulders, near the base of the neck. Morphologically, this signal corresponds roughly to a Lead I conventional ECG waveform, but with some distortion, and reduced amplitude. In a normal individual, it is characterized by a biphasic QRS complex and exaggerated T-wave. However, it is quite satisfactory for basic heart rate and rhythm monitoring. The signal amplitude is greatest when the electrodes are placed on the tops of the opposite shoulders, and gradually decreases as the electrodes are brought toward the base of the neck. The amplitude declines rapidly as the electrodes are moved up the sides of the neck, because only a rapidly attenuated fringe field exists within the neck itself.

The present invention is illustrated in FIG. 3. A monitoring electronics package 9 is attached to, and supported by, lanyard 10. Electronics package 9 hangs from lanyard 10 forming a V-shape system with the electronics package 9 at the vertex. A V shape is herein defined to include other similar shapes including a U shape. In the preferred embodiment, lanyard 10 is provided with two extensions or flaps 12, each of which carries an electrode 11 or other sensor. Lanyard 10 and flaps 12 are preferably dimensioned such that when hung around neck 54 of patient 50, electrodes 11 are located proximate to the base of patient neck 54, on opposite sides extending somewhat toward shoulders 56.

In an alternate configuration, flaps 12 may be dispensed with, and electrodes 11 placed on an inside surface of lanyard 10, such that they contact opposite sides of the base of neck 54. However, use of flaps 12 provides a more favorable location of the electrodes from the standpoint of signal amplitude, as has been discussed.

In the preferred embodiment, lanyard 10 is detachably connected to electronics package 9. The ability to detach lanyard 10 allows lanyard 10 and its integrated electrodes 11 to be made a disposable, or single-patient use component, while the electronics package 9 can be reused. A lanyard of sufficient length to comfortably encircle a person's neck will not necessarily pass over their head when formed into a closed loop. This problem could be resolved by making lanyard 10 of generous length, such that it will pass freely over the head. However, if lanyard 10 is made too long it will have a tendency to make the electronics package 9 become pendulous, which is undesirable. Therefore, it is preferable to have some means to open lanyard 10 so as to allow it to be wrapped around neck 54. In the preferred embodiment, this is accomplished by making ends 13 and 14 (seen in FIG. 4) of lanyard 10 detachable from electronics package 9.

FIG. 4 shows the preferred embodiment of the detachable lanyard assembly. Lanyard 10 includes two flaps 12, each bearing ECG electrodes 11, separated by a suitable distance X such that electrodes 11 rest approximately on top of a person's shoulders, proximate to the base of the neck, when lanyard 10 is closed or looped around the patient's neck.

The human neck varies significantly in size. In order for electrodes 11 to be positioned exactly consistently despite variations in neck size, variation of the electrode separation X is preferred. A length adjustment device 32 may be placed in the region between electrodes 11 to permit adjustment of distance X. Length adjustment device 32 may comprise an adjustable buckle. Alternatively, one portion of lanyard 10 may be provided with several perforations disposed along its length, any one of which can be mated with a corresponding stud on the other portion, effecting adjustment in length. The relative position of the portions can also be set by use of hook and loop fasteners, pressure sensitive adhesive, buttons, snap fasteners, or other similar means. The ability to adjust the length of lanyard 10 also proves useful when it is desired to deliberately alter the positions of the electrodes, as in cases where interference with a bandage, cast, or other medical device already placed on the patient must be avoided.

In an alternate embodiment, no buckle or other adjustment device is provided. Varying size requirements may be accommodated by manufacturing the lanyard 10 in various sizes, differing in dimension X. A small number of sizes is required to cover the entire range of neck sizes. A particular lanyard with a given dimension X will result in optimal electrode positioning for a certain neck size. If this same lanyard is placed on a subject with a considerably smaller neck, the electrodes will become displaced somewhat forward, moving down from the top of the shoulders toward the frontal surface of the chest. If this lanyard is placed on a person with a larger neck, the electrodes will be displaced from the top of the shoulders toward the person's back. However, neither of these displaced positions of the electrodes materially affects the quality or utility of the ECG signal obtained, provided the displacement is not very great. Therefore, a single size of lanyard can accommodate a considerable range of neck sizes, subject to acceptable displacement of electrodes 11.

In addition to providing superior support of the electronics, lanyard 10 of the present invention is generally of shorter circumference or length than belt 6 in an unfastened state, found in the prior art of FIG. 2. This is a consequence of the fact that the circumference of an individual's neck is considerably smaller than that of their torso. In cases where lanyard 10 is a disposable component, this results in a savings of not only the material used in construction, but also permits smaller and more convenient packaging and storage of the disposable component. The inclusion of electrodes 11 and associated conductors 16 within lanyard 10 additionally provides an advantage over the prior art of FIG. 2, where these components are part of electronics housing 5. Because electrodes 11 contact the patient, it is desirable that these components be disposable from the standpoint of sanitary practice. This is facilitated by their removal from the electronics housing and integration with lanyard 10.

Electrodes 11 may be of ordinary types, such as sponge or hydrogel types. However, unlike the prior art, they do not require a highly aggressive adhesive, as they are not required to support the weight of a heavy leadwire. The skin-contact surface of lanyard 10 itself and flaps 12 may be wholly or selectively coated with a mild adhesive, or may be coated with or comprised of material promoting friction or adhesion against the skin, to help prevent lanyard 10 from shifting in position and, thereby, mechanically straining electrodes 11.

Ideally, lanyard 10 should lie flat and conform to the body surface, without being twisted or buckled. An attempt to bend a flat, ribbon-like lanyard transversely will tend to cause it to buckle or twist. Therefore, rather than attempting to bend lanyard 10 to meet electronics package 9, electronics package 9 accepts ends 13 and 14 of lanyard 10 at their natural angle of approach. This is accomplished by providing for an articulating attachment of lanyard ends 13 and 14 to electronics package 9.

In FIG. 4, lanyard ends 13 and 14 are provided with central holes 17L and 17R, respectively, which engage an anchor post 28 (FIG. 5B) in electronics package 9. Ends 13 and 14 of lanyard 10 are free to pivot about anchor post 28, allowing accommodation for the natural angle of lanyard ends 13 and 14 when placed on patient 50. Adjustment of the attachment angle is only necessary at the time the device is placed on a person; at such time the angle should be set such that lanyard 10 lies flat and smooth. Once the angle is set, some degree of friction restricting further movement of the articulated connections is desirable, as this improves the mechanical stability of the device. It is preferred that the angle between lanyard ends 13 and 14, represented by arrow A, be adjustable by at least 15 degrees. Rotation of either or both ends 13 and 14 has the effect of changing angle A.

Lanyard 10 and flaps 12 may be composed of any material and have any accommodating geometry, however, a flexible ribbon-like material, such as fabric, textile braid, paper, soft plastic, or similar materials, or combinations of these materials, is preferred. Lanyard ends 13 and 14 may be stiffened, such as by lamination with stiff plastic sheet or heavy paper, to permit secure attachment to electronics package 9.

In the preferred embodiment, attaching lanyard ends 13 and 14 to electronics package 9 provides for both a mechanical and electrical connection. Mechanically, central holes 17L and 17R engage anchor post 28 (FIG. 5B) and ends 13 and 14 are enclosed in electronics package 9 in a clamshell manner (see FIG. 6B). Electrically, connection of electrodes 11 is provided by means of annular conductive contact regions 15L and 15R, which are connected to electrodes 11 by means of conductive paths 16L and 16R, shown as ghost lines, integrated into or otherwise attached to lanyard 10. At least a portion of one or both conductive paths 16 may be composed of a material having a high resistivity, such as carbon ink, so as to provide sufficient resistance in series with electrodes 11 as to facilitate protection of electronics package 9 from transient voltages induced in the electrode circuit during patient defibrillation.

Conductive paths 16R and 16L between electrodes 11 and electrical contact regions 15R and 15L are preferably integrated into lanyard 10, such as by lamination between layers comprising lanyard 10. Conductive paths 16L and 16R may take the form of a fine wire, a metal foil strip, a conductive polymer, conductive ink deposited by silkscreen or other printing process, or a flexible printed circuit board. Lanyard ends 13 and 14 may be composed of, or stiffened by, thin printed circuit boards, in which case the foil pattern of the circuit board may constitute contact regions 15L and 15R.

Electrical contact points 29 (FIG. 5B) connected to a circuit assembly 30 in electronics package 9 contact the conductive contact regions 15L and 15R, and thus provide a pathway between electrodes 11, which acquire the patient signal, to circuit assembly 30, which processes, stores or transmits the signal, or provides any combination of these functions.

According to the intended program of patient monitoring, electronics package 9 may be designed to accomplish any of a number functions. For example, it can operate in the manner of a holter monitor, where it only stores patient signals. It could operate in the mode of a conventional telemetry transmitter, where the full waveform of the patient's signal is transmitted to a remote location. It could alternately operate in the mode of an exercise monitor, in which the heartbeat is detected, and a signal marking each heartbeat is transmitted to a remote device. Further, it could operate by locally processing and analyzing the patient signal, and transmitting only summary data or analysis results to a remote device. Note that not only the ECG, but any signal related to cardiac activity, such as the photoplethysmograph signal, heart sounds, mechanical pulse signal, and others can be used as the basis for detecting the heartbeat. Further, by the introduction of other sensor types in addition to, or instead of, electrodes 11, other types of physiologic signals may be stored or manipulated by electronics package 9, as described for the ECG signal.

End 13 or 14 of lanyard 10 may include a battery 18, or alternate power source, to run the device. In the preferred embodiment, the battery is a lithium coin cell, such as the standard type CR2032, produced by numerous manufacturers. However, the use of other types of batteries is contemplated, including multiple cells in series or parallel, other chemistries such as zinc-air, and other planar battery structures, such as the flat Polapulse batteries manufactured by Polaroid Corporation (Waltham, Mass.).

Alternately, battery 18 may be incorporated into electronics package 9. However, in the preferred embodiment, the battery is attached to the disposable lanyard 10, so that a fresh battery is automatically provided when a new lanyard 10 is placed on a patient and connected to electronics package 9. Since lanyard 10 may be designed for single patient use, a number or other identifier assigned to the lanyard 10 at the time of manufacture becomes a convenient patient identifier. In the preferred embodiment, this identifier is stored in electronic form, and can be automatically read from lanyard 10 by electronics package 9.

FIG. 5A illustrates the details of the preferred embodiment of lanyard ends 13 and 14. End 13 comprises a battery 18, an electronic identifier 19, an upper surface 13US, a lower surface 13LS, a central hole 17L and annular electrical contacts 15L, 20 and 21. End 14 comprises an annular electrode contact 15R, an upper surface 14US, a lower surface 14LS, a central hole 17R and annular slots 22A, 22B, 22C and 22D. Lanyard ends 13 and 14 are shown positioned as they would be after looping lanyard 10 around the neck of a person but before being connected to electronics package 9, i.e. surfaces 13US and 14US both face up.

Identification device 19 is preferably an electronic memory device, such as the DS2401 Silicon Serial Number, manufactured by Dallas Semiconductor (Dallas, Tex.). This device contains a unique identification number which can be read electronically by a single wire serial data interface, established preferably through contact 21. The common or ground connection used by this device may be made by means of the battery contact or electrode contact 15. Other types of memory devices may be used. Although the DS2401 requires no explicit power source, battery 18 may supply standby power to other types of identification devices. For example, a device utilizing static RAM for data storage could be kept energized, even when not connected to electronics package 9, by means of battery 18.

Annular contact segments 15L, 15R, 20 and 21 may take the form of a metal foil, conductive polymer, or conductive ink, deposited by silkscreen or other printing process, or any other appropriate conductive contact known in the art.

Lanyard ends 13 and 14 could be placed in the electronics package 9 side by side, much as they are illustrated in FIG. 5A, on independent anchor posts. However, the preferred embodiment makes use of a common anchor post 28, as is shown in FIG. 5B. This figure shows ends 13 and 14 of lanyard 10 placed into opened electronics package 9 for the purpose of attaching it to lanyard 10. Electronics package 9 consists of a cover 23 and body 24 connected by hinge 25, and is capable of being closed and secured by latch tongue 26 and latch receiver 27, in the manner of a clamshell.

End 14 is placed over end 13, i.e., end 13 is sandwiched between end 14 and cover 23. Cover 23 is provided with anchor post 28, which engages the central holes 17L and 17R of ends 13 and 14. End piece 13, containing contacts 15, 20, and 21, is first placed over anchor post 28 in housing cover 23. Next, end piece 14 is placed over end piece 13 by disposing anchor post 28 within central hole 17R. End piece 14 is provided with suitable apertures 22A-22D which permit access to the contact regions 15, 20, and 21, as well as the terminal area of battery 18. The opposing half of the electronics package housing, base 24, is provided with several electrical contact points 29, connected to circuit assembly 30, which contact the various electrical contact regions of end pieces 13 and 14 when electronics package 9 is closed, i.e., when latch tongue 26 snaps over or mates with latch receiver 27. Battery 18 is shown in ghost lines as it is underneath end piece 14, although accessible to electrical contact through aperture 22B. Contact regions 15L, 15R, 20 and 21, and apertures 22A-22D, have annular shapes but may take on other shapes so long as they are suitably dimensioned to permit articulation as discussed above, such that some portion of each annular contact region is accessible to its corresponding contact point 29 over a predetermined range of angular rotation of ends 13 and 14 about anchor post 28.

Figure 6A:
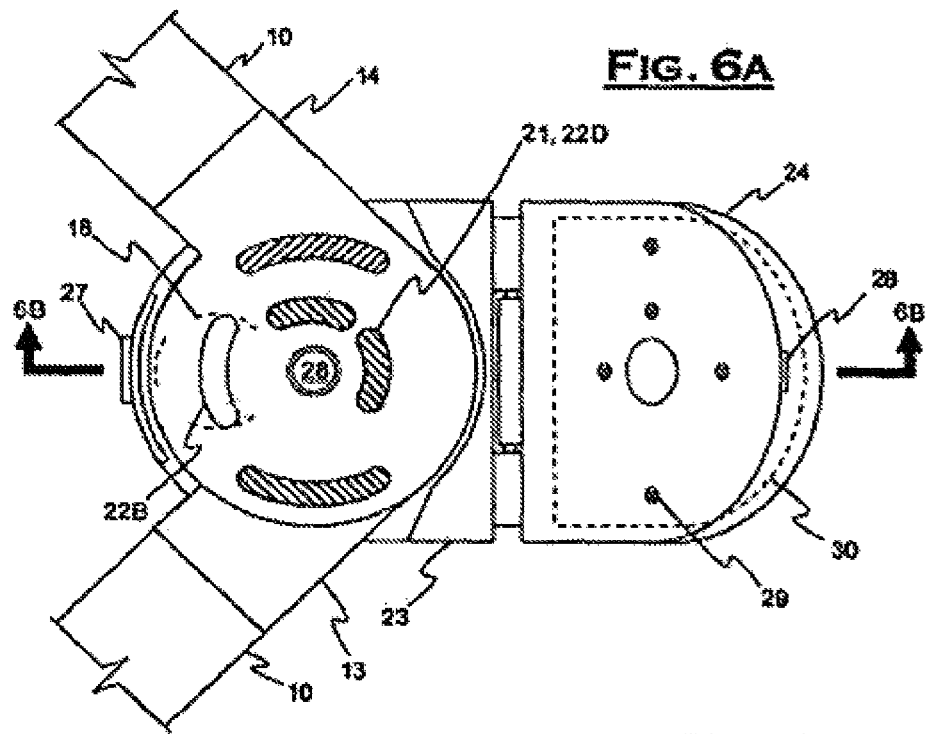
FIG. 6A is a plan view of the ends of the lanyard and the partially closed electronics housing.
Figure 6B:
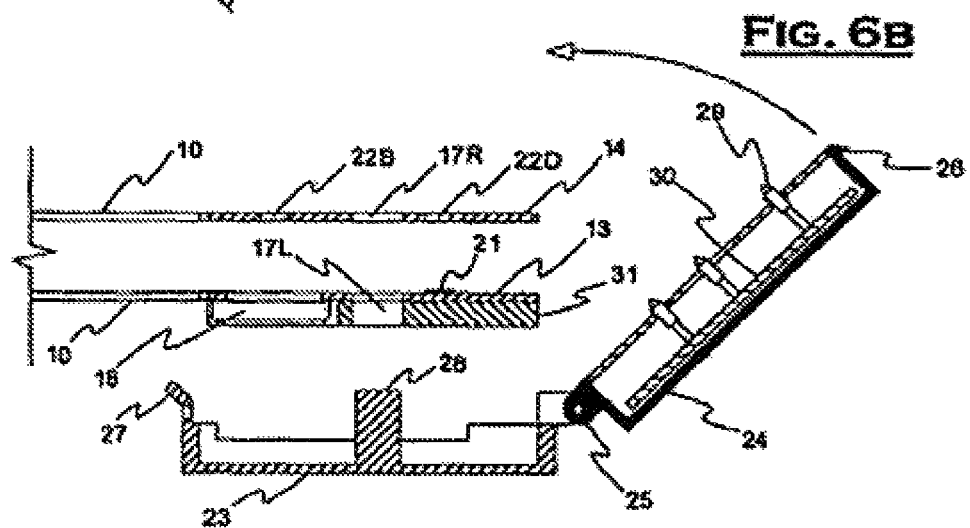
FIG. 6B is a longitudinal cross-sectional view of the ends of the lanyard and housing taken along lines 6B-6B of FIG. 6A.

FIG. 6A shows another view of the end pieces in electronics package 9, shown in a partially closed position. A sectional view along lines 6B-6B, clarifying the arrangement of the components, is illustrated in FIG. 6B. For clarity, ends 13 and 14 have been shown lifted out of housing cover 23 in the sectional view. To complete attachment of electronics package 9 to lanyard 10, end pieces 13 and 14 would be dropped fully down over anchor post 28, and housing body 24 pivoted on hinge 25 in the direction indicated by the curved arrow, until electronics package 9 is closed, and latch tongue 26 becomes retained in latch receiver 27. This operation brings contact points 29 to bear on their associated annular contact regions on ends 13 and 14. The sectional view cuts through annular contact 21 and battery 18, located on end 13. Note that apertures 22B and 22D are provided on end piece 14 directly above these components to permit access by the associated contact points 29. To provide a flat surface on end piece 13, despite the thickness of battery 18 and identification device 19, spacer disk 31 may be attached to end piece 13. Spacer disk 31 may be cut out to accept the thickness of battery 18, identification device 19, and any other auxiliary components which may be attached to end piece 13.

Several variations of the construction depicted in the figures are possible. Anchor post 28 may advantageously be made considerably longer than is necessary to engage both central holes 17R and 17L, as the additional length helps the user to position the end pieces over anchor post 28 and maintain them in position while closing electronics package 9. A suitable recess may be required in housing body 24 to receive the excess length of anchor post 28. The construction can also be inverted, in which anchor post 28 projects from housing body 24. In this case, ends 13 and are first dropped over anchor post 28 protruding from body 24, and then cover 23 is closed over them. Alternatively, it is possible to dispense with central holes 17R and 17L and anchor post 28 altogether, and rely on the circular portion of the outer periphery of ends 13 and 14, together with the internal shape of cover 23, to locate ends 13 and 14 while still allowing articulation.

To aid in keeping end pieces 13 and 14 correctly positioned within housing cover 23, various retention features may be added. For example, anchor post 28 may be furnished with an undercut, barbs, or similar feature which catches central holes 17R and 17L of ends 13 or 14. Alternatively, central holes 17R and 17L and anchor post 28 may be dimensioned to provide a snug fit. Also, ribs or projections may be added to an internal periphery of housing cover 23 to assist in retaining ends 13 and 14 by engaging their outer periphery.

Hinge 25 may take various forms, including a living hinge integral with the plastic comprising electronics package 9. Electronics package 9 may be constructed without a hinge, as illustrated in FIG. 7. In this case, body 24 and cover 23 are not hinged together, but are separate components. Ends 13 and 14 are first dropped over anchor post 28 of housing cover 23 and then housing body 24 is engaged by perpendicular motion, as indicated by the arrow in the figure, and becomes secured by latch tongues 26 and latch receivers 27. To avoid accidental loss of cover 23, it can be integrated with the disposable lanyard assembly. For example, it can be made a captive part of end piece 13, while still allowing the angular rotation necessary for articulation. For either construction, latch tongue 26 and latch receiver 27 may be replaced by any of several well-known closure devices. These include threaded fasteners, cam or "quarter-turn" fasteners, magnetic catches, friction locks, pressure sensitive adhesives, hook and loop fasteners, or any similar devices. More than one latching point may be provided. The location of the latching point may differ from that shown, such as by being located in the center, rather than periphery, of the housing.

The identifier stored in identification device 19 may also be printed on a label affixed to lanyard 10. This label may be human readable, machine readable, as in the case of a bar code, or both. Such a label may be placed anywhere on the device. However, in the preferred embodiment, it is placed on the underside of spacer disk 31, as seen in FIG. 6A, 6B or 7. Cover 23 may be composed of a transparent material, or furnished with a window, such that the label can be read through the cover while the monitoring device is worn by a person. In this case, electronics package 9 also serves the purpose of an identification badge or pendant. In the arrangement shown in FIG. 7, cover 23 may be integrated with end piece 13, as has been discussed. In this case, cover 23 need not be transparent or windowed, as the identification label can be placed on an outer surface of captive cover 23.

The need for apertures 22A-22D may be eliminated if contact points 29 are provided on cover 23 as well as body 24 of the electronics package housing. The annular contact regions 15L, 20 and 21 of end 13 would then be placed on surface 13LS, as opposed to surface 13US, such that they touch the contact points provided in cover 23. In this case the spacer disk 31 may advantageously be placed between ends 13 and 14.

In an alternate embodiment of articulated ends 13 and 14, annular contact regions 15L, 15R, 20 and 21 are eliminated, and anchor post 28 becomes the contact and mates with a receptacle in electronic package 9. Various forms of this arrangement, differing in the number of contact circuits provided, are shown in FIGS. 8A-8C.

FIG. 8A illustrates lanyard 10 attached to modified end 36, equipped with an electrically conductive contact stud 37. Stud 37 serves both the function of an anchor post, allowing articulation, and an electrical contact. Although the figure shows the male portion of the connection on end 36, and presumes the corresponding female portion to be on electronics package 9, it is understood that the configuration may be inverted, with the male portion on electronics package 9 and the female portion on end 36. The male and female portions may take on various particular shapes. For example, stud 37 may assume the form of the male portion of a snap fastener and the receptacle the mating female portion of a snap fastener. The arrangement shown in FIG. 8A is suitable when only a single circuit is to be connected, for example, from an electrode. When multiple connections are required, the simple stud may be replaced by a coaxial contact arrangement.

FIG. 8B illustrates a lanyard end 36 with a stud 37, now having a coaxial contact. Stud 37 comprises an outer contact portion 38 and an inner contact portion 39, permitting two circuits to be connected.

FIG. 8C illustrates a lanyard end 36 having a stud 37 divided into several contact rings 40, separated by insulating regions 41, in the manner of an ordinary headphone plug. Although the figure shows three circuits, it is understood that more or fewer circuits could be provided.

Planar ends 13 and 14 with the several annular contact regions of the preferred embodiment facilitate provision of large numbers of contacts, such as when auxiliary components must be provided with contacts in addition to electrodes. However, the alternate embodiments of FIGS. 8A-8C, while more restricted in the number of contacts, are better adapted to waterproof or water resistant construction. Hybrid constructions employing both a central contact stud of any of the forms discussed, plus one or more annular contact regions on the face of end 36, are anticipated as well.

Whenever any lanyard is placed about a person's neck, the risk of accidental strangulation or other injury must always be considered. Should the lanyard become entangled or otherwise engaged with some other object, machinery, or the like, injury may result. In order to prevent such injury, lanyard 10 may be designed with a breakaway feature, such that this feature becomes disengaged before a dangerous degree of tension can be produced in lanyard 10.

There are many commonly known methods of providing a breakaway feature. The tensile strength of the lanyard material can be selected so as to avoid danger. If lanyard 10 is composed of a stronger material, it can be equipped with a weakening notch or perforations designed such that the area so weakened will fail at the desired tension. Length adjustment device 32 can be designed to release or fail at a predetermined tension. The strength of attachment of lanyard 10 to ends 13 and 14, or the strength of ends 13 and 14, can be suitably chosen. Furthermore, the engagement of lanyard ends 13 and 14 into electronics package 9 can be designed to release or fail at a predetermined tension.

The use of a flat, ribbon-like lanyard 10 provides good mechanical stability of the invention when placed on a person. Further, it affords the possibility of coating the skin-contact side of lanyard 10 with adhesive or friction-promoting material, further enhancing stability. However, a lanyard of substantial width does not flex readily transversely. Accordingly, if such a lanyard is to lie flat and smooth, the attachment of the lanyard to the electronics unit 9 should be articulated, as discussed. The articulated attachment adds some degree of complexity, particularly if waterproof or water resistant construction is required.

In contrast to a ribbon, a thin cord, particularly one of circular cross-section, flexes with equal ease in all directions. If lanyard 10 were constructed of such a cord, articulated connections to electronics package 9 would no longer be required, as the cord could easily flex to meet attachments of some fixed angle.

It is possible to construct the entire lanyard assembly of such a cord. However, some measure of the mechanical stability afforded by the flat ribbon can be preserved by a composite construction. An alternate embodiment of the invention incorporating such a composite construction is illustrated in FIG. 9. Lanyard 10 consists of a flat ribbon portion 42 and two flexible cords 33L and 33R. As in the other embodiments, lanyard 10 is furnished with electrodes 11, or other sensors, and may additionally have flaps 12. Lanyard 10 may also be furnished with length adjuster 32. Cords 33L and 33R may be provided in various ways. A cord or tubing may be attached to the flat ribbon portion 42 of the lanyard 10. Alternately, flat ribbon portion 42 itself may be folded, rolled, or twisted into a tube on the ends.

Cords 33L and 33R each contain a suitable electrical conductor for electrodes 11, as well as any other electrical devices attached to the lanyard assembly. Cords 33L and 33R are equipped with connectors 34L and 34R on one end, which mate with sockets on electronics package 9, providing electrical and mechanical attachment. Connectors 34L and 34R may use any of the common forms of electrical contacts, such as pin and socket, butt, bellows, and others familiar to those skilled in the art. Any of several common retention means, including friction, detent, threads, bayonet, and similar means may be used to secure connectors 34 into electronics package 9. Auxiliary devices, such as battery 18 or identification device 19, may be imbedded in connectors 34, or located elsewhere on the lanyard assembly, and provided with suitable conductors to, and contacts in, the connectors. The use of two connectors 34L and 34R permits lanyard 10 to be opened for ease of placement about the neck, and therefore allows for use of a lanyard too short to pass over the head when closed.

In FIG. 10, a single common connector 35 to electronics package 9 is used, with both cords 33L and 33R attached to this single connector. In this case, lanyard 10 may be made long enough to always be capable of passing over the head, or alternate means of opening the lanyard may be provided. Length adjuster 32 may provide the means of opening the lanyard, or a similar device not providing length adjustment, but merely allowing lanyard 10 to be separated, may be employed. Alternately, one of cords 33L and 33R may be made detachable from common connector 35. Although the preceding examples have shown only two electrodes 11 as the physiological signal sensors, other configurations are anticipated, and additional sensors may be added. While ECG signal acquisition without a reference electrode is possible, certain applications of the invention may benefit from the improved signal possible with such an electrode. A third electrode may therefore be placed at any convenient skin-contact location on lanyard 10, and be furnished with suitable conductors to, and contacts in, the end pieces. Similarly, the lanyard assembly may be furnished with additional active electrodes 11 and longer flaps 12, such that these electrodes may be placed on various portions of the chest, such as to approximate conventional three or five electrode monitoring configurations.

Other types of sensors, besides ECG, are contemplated as part of the invention. A portion of the lanyard 10 contacting the skin may be furnished with a thermistor or other temperature sensor, allowing the body temperature to be monitored. A portion of lanyard 10 contacting the skin may be equipped with a reflectance mode pulse oximetry sensor, allowing the patient's blood oxygen saturation to be monitored. Alternately, an extension, similar to flaps 12, may be added to integrate a transmission mode pulse oximeter sensor placed on the earlobe. A similar extension may be used to integrate various sensors placed within the ear canal, such as a tympanic temperature sensor or ear canal pulse oximeter. In all cases, additional sensors are provided with suitable conductors in lanyard 10, and contacts in the end pieces, allowing their signals to be communicated to electronics package 9.

Electronics package 9 may also be furnished with various sensors in addition to the customary signal processing and related electronics. For example, an accelerometer and inclinometer may be provided to detect activity and posture of the patient, providing useful information for correlation with the other vital signs.

While the preferred embodiments comprise a disposable, or single-patient use, lanyard assembly and reusable electronics package 9, the ever-lowering cost of electronics makes a fully disposable device feasible in certain applications of the invention. In this case, electronics package 9 need not be detachable from the lanyard 10, and the complexity of connectors 34L and 34R may be eliminated. If the lanyard is made sufficiently long to pass over the head when formed in a closed loop, all means of detachment of any portion of lanyard 10 may be eliminated. If a shorter lanyard, which must be opened to pass over the head in at least some cases, is to be used, at least one point of detachment must be provided. This may be combined with length adjustment device 32, and need not involve the interruption of any electrical conductors.

Lanyard 10 and electronics package 9 are preferably arranged such that the electronics become active, such as by connection of battery 18, automatically only when the detachable portions of the lanyard are engaged. In this way, no drain of the battery can occur before the device is placed on a person, and the device is automatically set in action once placed on a person. This occurs naturally with the construction illustrated in FIG. 5, since battery 18 makes connection with the electronics package 9 when the electronics package housing is closed about ends 13 and 14 of the lanyard 10. However, this feature may be provided in other constructions by arranging any attachment point to close an electrical circuit when engaged, such as by closing a switch, or by engagement of electrical contacts and conductors carried through the attachment point.

A mobile patient monitoring system 100 according to another embodiment of the present invention will now be described with reference to FIGS. 11-13.

Figure 11:
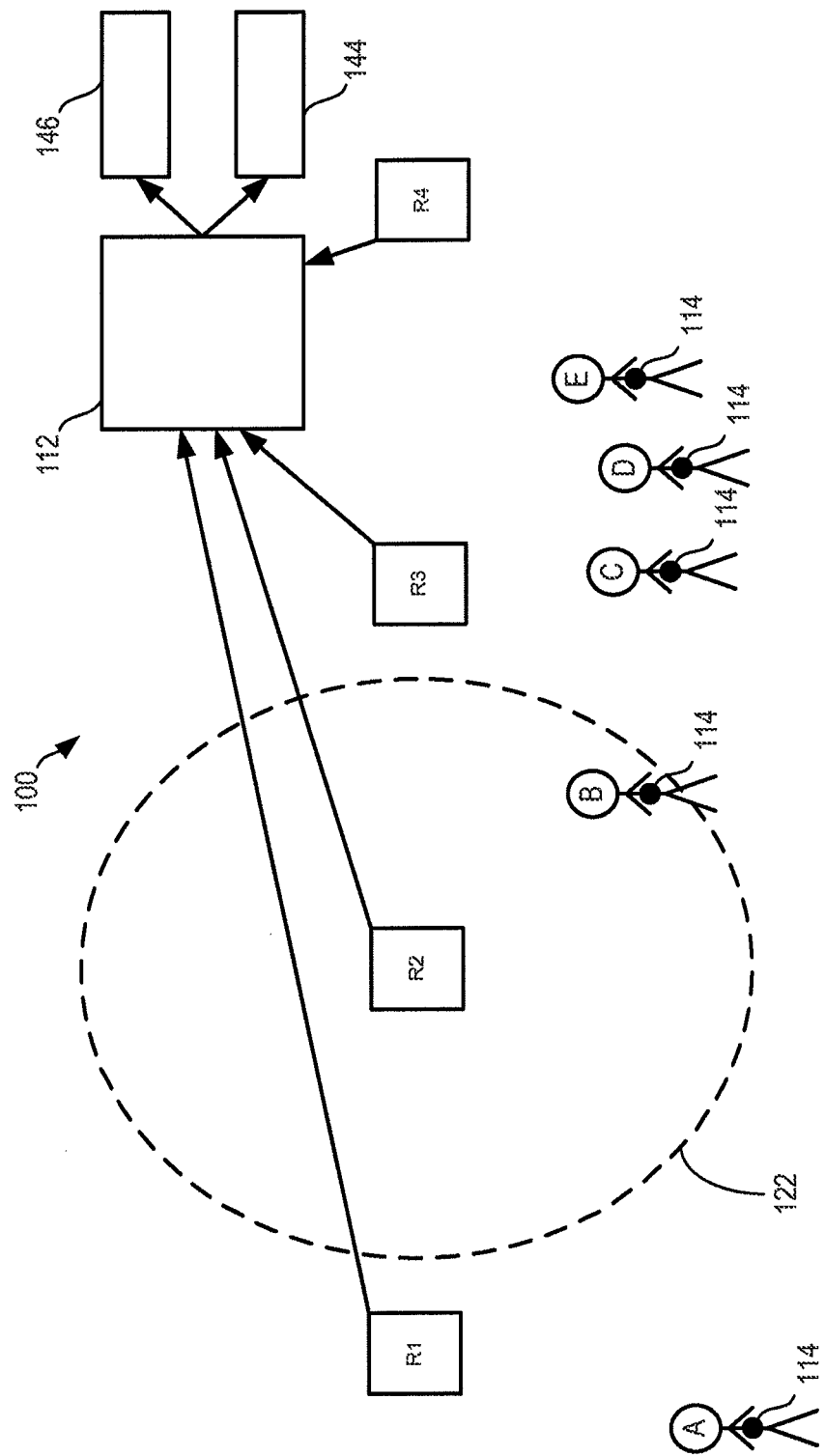
FIG. 11 is a block diagram of another embodiment of a mobile monitoring system of the present invention, showing the relationship of several patients to multiple receivers.

An overview of a preferred embodiment of the system 100 is shown in FIG. 11. System 100 consists of a central station means 112 linked to a series of receiving means, labeled R1-R4, distributed throughout a defined area, such as the patient areas of a hospital. Each of five patients, labeled A-E, have an associated transmission means 114 for acquiring his or her physiological signal, processing it to obtain medical condition data, and then transmitting this medical condition data to one or more of the receiving means R1-R4 for transmission to central station means 112. The physiological signal acquired may be the patient's ECG waveform and the medical condition data may consist of heart rate and rhythm.

Note that transmission means 114 may vary depending on the type of subject and range of conditions being monitored. The present invention is not limited to monitoring cardiac health of a patient in a hospital setting. One may want to track the movements of a turtle in a defined area, for example, and monitor the water content of its shell.

In the preferred embodiment, however, transmission means 114 is adhered to a patient's chest and includes a device capable of measuring a patient's physiological signals, such as the ECG signal, and analyzing these signals for patient medical condition data, such as heart rate and rhythm. More specifically, one transmission means 114 is connected to each patient A through E.

Figure 12:
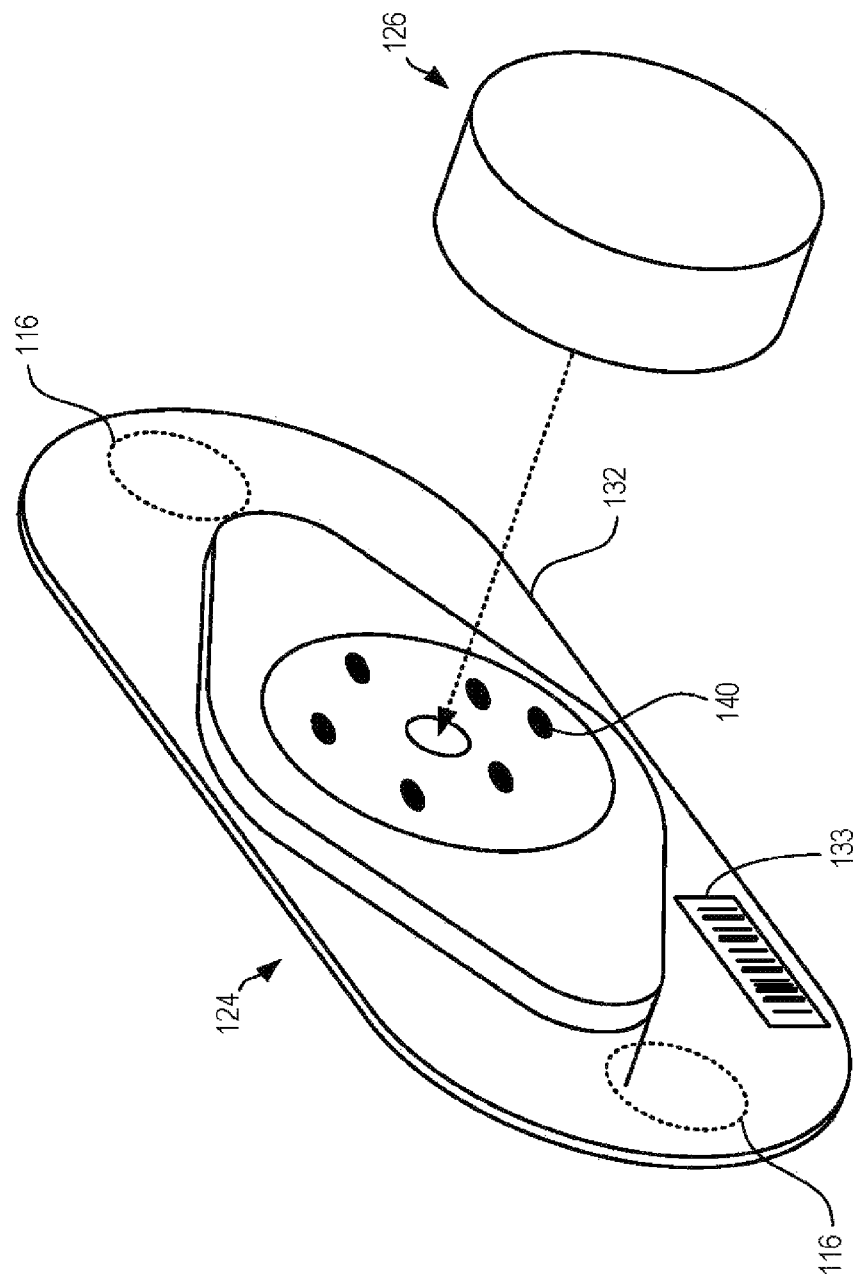
FIG. 12 is a perspective view of the patient transmitter according to the present invention.
Figure 13:
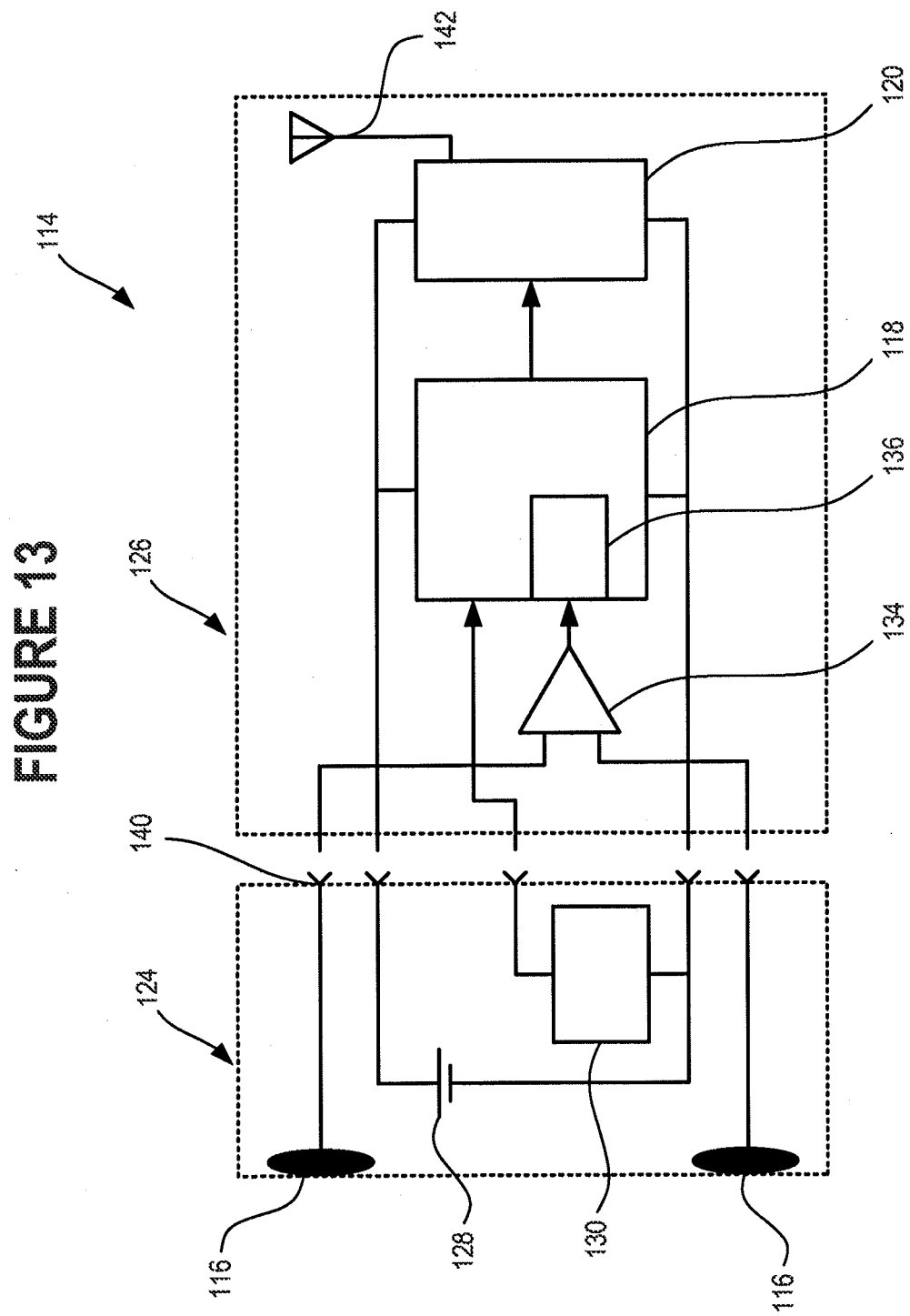
FIG. 13 is an electronic block diagram of the patient transmitter of FIG. 12.

In general, transmission means 114 includes a signal sensing means 116, a computing means 118, and a transmitter 120 (see FIGS. 12 and 13). Signal sensing means 116 may include one or more electrodes (as illustrated in FIGS. 12 and 13), a plethysmograph sensor, or other heart beat detection means. Computing means 118 analyzes a subject signal and produces patient condition data based on the subject signal. Computing means 118 may include a microprocessor, microcontroller, ASIC, or other programmable logic. Transmitter 120 transmits the patient condition data to central station means 112. Transmitter 120 may include a radio frequency, infrared, or ultrasonic device, or other device known in the art capable of transmitting bursts of data. The preferred embodiment of transmission means 114 is detailed below.

Receiver means R1-R4 may include any device known in the art capable of receiving bursts or a stream of data and communicating this data to central station means 112. In this example, receiver means R1-R4 include a radio frequency receiver, means for communicating with central station means 112, and computing means (all not shown). The computing means may include a microprocessor, microcontroller, ASIC, or other programmable logic. Means for communicating with central station means 112 may include any of various computer data network communication devices, such as a wireless network, or a wired network having either star, multidrop, or ring topology.

Central station means 112 may include any device capable of receiving and analyzing bursts or streams of data. Central station means 112 monitors each patient's medical condition data for predetermined rate and rhythm alarms. When an alarm condition is detected an alert is sounded or displayed on an associated display (not shown). Central station means 112 may also be configured to directly summon a response team, by means such as an interface to a telephone or pager system. By identifying the particular receiving means R1-R4 picking up a given patient's signal, the patient's location is known. Central station means 112 may include custom software running on a PC, equipped with suitable commercial wired or wireless network connectivity, or other computing platform.

Note that despite system 100's optimization to work for short bursts of data, as opposed to extended or continuous signals, due to interference concerns, central station means 112 may receive and analyze continuous physiological signals.

As indicated above, FIG. 11 illustrates a schematic representation of system 100 of the present invention. Five patients, labeled A through E, are being monitored by four receiving means, designated R1 through R4. Note that the number of patients and receiving means may vary and that the numbers used in this example are for illustration purposes only. Each receiving means has a coverage radius overlapping that of at least an adjacent receiving means, as is illustrated by the dotted circle 122 surrounding receiving means R2. In the example illustrated in FIG. 11, patient A is in range of only one receiving means, namely, R1. However, patient B is in range of both receiving means R2 and R3. Further, receiving means R3 may also be receiving signals from patients C, D, and E. Patient E is also in range of receiving means R4. As a patient moves, his signal will pass out of range of his original receiving means, and into the range of an adjacent receiving means, with some overlap.

System 100 of the present invention is designed so as to handle patients within range of two or more receiving means at one point and designed such that patient condition data from multiple patients arriving at a single receiving means will not interfere with each other. The system is also designed such that there is no loss of data or manual intervention necessary as a patient moves from one receiving means to the next. Furthermore, transmission means 114 may include in the patient condition data information relating to the patient's identity, since it is not known in advance where each patient's signal will be received.

Some known telemetry systems require bi-directional communication to manage the communication process itself. For example, in some known systems a central point sends a polling request to interrogate each remote unit, which then responds with data, as a means of allowing multiple devices to share a single channel. In order to minimize power and complexity, the present system uses unidirectional communications only, but at the expense of losing some ability to manage the communication process.

The present invention is a successfully designed mobile patient monitoring system 100, employing a unidirectional system, with minimal interference issues. Interference is minimized by transmitting to central station means 112 patient condition data, i.e. vital signs, rather than the patient's physiological signal, i.e. ECG waveform. Information is transmitted in short bursts, at low duty cycle, to minimize interference, i.e. information from different patients arriving at a single receiving means at the same time. In contrast to ECG waveforms, the amount of data associated with vital signs is small and changes slowly, and thus is amenable to short burst transmissions. Further, given that vital signs, such as heart rate and rhythm, are based on averaging information from several heart beats, and thus do not change instantaneously, it is adequate to update the data only every second or two. This is in contrast to ECG waveforms which need to be updated much more frequently to maintain a smooth waveform. Note that occasional interference of patient data does not significantly affect the monitoring value of the present system because data updating is quite redundant; that is, the loss of an occasional update does not severely limit the value of the data, and adequate information can be obtained by simply waiting for the next update. Given this, it is not necessary to request that the lost data be retransmitted.

In accordance with the above, present system 100 uses multiple transmission means 114, which use the same channel but without any coordination, i.e. they are variable in timing and asynchronous. In other words, one patient transmission means transmits bursts of data to receiving means without any attempt to assure that another transmission means is not transmitting at the same time. While this may result in occasional interference between competing transmission means 114, and therefore occasional loss of data, with this type of interference being sufficiently rare it is not objectionable.

Each cycle has an active phase in which energy modulated with the patient condition data is emitted and a longer inactive phase in which no energy is emitted. To avoid overlap of the active periods, the duration of the active phase should be less, and preferably much less, than the period of a complete cycle divided by a predetermined maximum number of transmission means anticipated to be within range of any one receiving point at any one time. The shorter the active phase is made, the less the probability of overlaps and associated interference.

As indicated above, in order to minimize interference, transmission means 114 sends updates as short bursts of data, preferably lasting approximately 5 milliseconds, with bursts of data at intervals averaging one second, with a random variation. Thus, transmitter 120 is in an active phase only about 0.5% of the time. If two such transmission means, without any synchronization between them, are sharing a single receiving means, there is a small probability that they will occasionally interfere, with the result that they both lose one update. However, because of the randomness of the time to the next update, it is highly unlikely that they will lose the next update as well. In the very unlikely event that this happens, there is an even smaller, essentially negligible, probability that this would happen a third time. Therefore, the worst that could happen as a result of the mutual interference of these unmanaged transmitters 120 is a rare delay in the data update by a second or two at most. As more similar transmission means are brought into range of this one receiving means, the probability of interference increases, but since the patient transmission means is designed with a short range, it limits the number of transmission means 114 that can be within range of each receiving means R1-R4, while at the same time reducing power consumption.

Transmission means 114 operate on a duty cycle which is determined by taking into consideration and optimizing the following variables: (a) the amount of patient condition data that must be transmitted; (b) the speed of the transmission; (c) how often the patient condition data must be sent; (d) the allowable number of transmission means that can be in range of a receiving means at once; (e) the spacing of the receiving means; (f) the acceptable rate of patient condition data loss; (g) overhead associated with transmission of the burst of patient condition data; and (h) the average repletion rate of the data bursts.

The data to be transmitted preferably includes the patient's rate and rhythm information, as well as a patient identification, the technical status of the transmitter, and error-checking information. The heart rate is a number in the range of 0 to perhaps 300, and therefore can be represented in 9 bits of information. In addition to this, a few flags or codes are desirable to indicate rhythm alarms. Therefore, the patient heart rate and rhythm information will fit in two bytes, or 16 bits. Allowing 3 bytes for the patient identification provides over 16 million unique identification possibilities. The technical status needs only a few indicators such as low battery or electrode faults, so one byte is adequate. Finally, one byte can be used for error checking. Therefore, a total of 7 bytes, in this example, are transmitted by transmission means 114.

A certain amount of time is required to power up and stabilize transmission means RF transmitter 120, as well as to shut it down. The above-described data is framed in such a way that receiving means R1-R4 can synchronize to the burst of data from transmission means 114 and extract individual data fields. The data framing consists of two parts. The first is the preamble, which contains some void data bytes to allow receiving means R1-R4 to stabilize and synchronize on the incoming data. This is followed by a header, which contains an unambiguous marker of the start of the data. The header function can be achieved in two bytes, and 4 bytes is a reasonable length for the preamble, although this is strongly dependent on the receiver technology adopted. Therefore, an additional 6 bytes, plus the power up and power down time of transmitter 120, are required.

Based upon the above, it is preferred that 13 bytes be transmitted by transmission means 114. Although each byte contains 8 bits of data, it actually requires 10 bits to transmit in asynchronous format. The time this takes depends on the data rate, and thus, on the transmission means transmitter 120. One available commercial miniature transmitter module has a maximum data rate of 115,200 bits per second, and could send this data in 1.13 ms. However, higher link reliability in the face of noise and interference can be achieved by using less than the maximum data rate. Therefore, as an example, if the data is sent at one quarter of this rate, 4.51 ms is required. This same transmitter module takes less than 50 µs each to power up and down, making the total transmitter "on" time 4.61 ms.

An interval of one update per second is more than adequate. For example, most bedside monitors only update their numeric displays at 2-second intervals. Therefore, the transmitter would operate at a duty cycle of 4.61 ms out of every second, or about 0.5%. This duty cycle is low enough that the other aspects of the compromise, relating to interference as discussed above, are not difficult to maintain. Further, this very low duty cycle is helpful from the standpoint of battery life, since it means that very little average power is required for the transmission means transmitter 120. If more data were to be sent in each burst, such as a rudimentary waveform, the duty cycle would become greatly increased. For example, if an ECG waveform sampled at 100 points/second (corresponding to a poor recording) were to be continuously sent, the duty cycle would increase to almost 4%. This would greatly increase the probability of interference between transmitters 120 and lost data. However, because the waveform is not as redundant as the simple numerical data, the impact of occasional lost data is much greater. Given the problems with transmitting full waveforms, representative samples of a waveform may be transmitted at certain times. In particular, such a sample can be taken at the time an alarm condition is detected.

FIG. 12 illustrates a perspective view of the preferred embodiment of the patient transmission means 114, which includes a subject portion 124 and a transmitter portion 126, both of which are circumscribed by broken line boxes in the block diagram of FIG. 13.

Subject portion 124 of transmission means 114 includes signal sensing means, such as ECG electrodes 116, a power supply 128, patient identifier means 130 and a support 132 (FIG. 12), which is preferably adhesive and disposable.

Power supply 128 may include a battery, for example, lithium coin cells. These cells take the form of a flat disk, similar in size to a stack of one or two quarters. Patient identifier means 130 may include a device containing a numerical identifier, or serial number, such as a memory device, for example, a serial PROM. Since power supply 128 may be part of subject portion 124, a fresh power supply 128, preferably a battery, is automatically provided for each patient. The device is activated when transmitter portion 126 is attached to subject portion 124.

FIG. 13 is a block diagram of transmission means 114 showing the internal parts of transmitter portion 126 and subject portion 124.

Transmitter portion 126 may be removably connected to subject portion 124. The patient's ECG is picked up by electrodes 116, passed through an amplifier 134 and into a computing means 118 and an analog-to-digital converter 136. Computing means 118 may include a microprocessor, microcontroller, ASIC, or other programmable logic. A number of electrical contacts 140 are provided as part of subject portion 124 so that the reusable transmitter portion 126 can be attached thereto, mechanically as well as electrically. Patient identifier means 130 is also connected to computing means 118. Computing means 118 performs an analysis and outputs patient condition data to RF transmitter 120 which has an associated antenna 142 for broadcasting the patient condition data, according to the telemetry scheme outlined above.

ECG electrodes 116 are just a few inches apart on support 132. While this does not provide a conventional ECG vector (for example, lead II), it does provide a signal that is useful for basic rate and rhythm measurements. However, should this signal be inadequate, there may be modifications to the structure that will allow a conventional electrode placement to be used. For example, the second electrode could be located remotely and connected by a wire to support 132. However, the use of closely spaced electrodes on a single support provides a desirable simplicity and a clean design.

Alternatively, subject portion 124 may be configured as a belt wrap. In this case, wider electrode spacing, approximating a conventional Lead I ECG, is possible.

Patient identifier means 130 may include a tiny inexpensive integrated circuit encoding a unique serial number and patient ID for each support. Such devices are available commercially with unique serial numbers already installed by the manufacturer, such as the "Silicon Serial Number" made by Dallas Semiconductor (Dallas, Tex.). When the adhesive support 132 is manufactured, the imbedded serial number integrated circuit is interrogated, and a matching number is printed on bar code label 133 attached to support 132 to facilitate patient admission.

Off-the-shelf technology is available for RF transmitter 120. For example, RF Monolithics (Dallas, Tex.) manufactures very small RF transmitters that require only a few tiny support components. Their TX6000 series measures nominally 7 mm by 10 mm by 2 mm, and incorporates the entire RF function except for the antenna. Other manufacturers offer similar products.

As indicated above, a microcontroller chip may be used for transmitter portion computing means 118. These chips often include an internal analog to digital converter of suitable quality for acquiring the ECG signal. The chip should be computationally powerful enough to analyze the rhythm of the acquired patient ECG signal. While rhythm analysis is a complex subject, in this case the primary goal is to reliably identify lethal arrhythmias, in particular, those rhythms that would be considered "shockable" by an automatic external defibrillator (AED). Poor specificity between different types of lethal arrhythmias is not of great concern, since the response to any such arrhythmia is likely to be the same, the dispatch of an intervention team. Algorithms far simpler than those used for complete rhythm analysis can be used to identify shockable rhythms, such that satisfactory rhythm identification can be performed with a fairly simple and low power microprocessor. In general, such simplified algorithms concentrate on the timing of the heart beats, rather than the details of their morphology. For example, the arrhythmias of ventricular tachycardia and ventricular fibrillation may be identified on the basis of high apparent heart rate, without making an effort to distinguish between them on the basis of waveform shape, as in both cases an alarm condition would be declared. Potential devices include various members of the PIC family made by Microchip (Chandler, Ariz.), AVR devices made by Atmel (San Jose, Calif.), and 430 series microcontrollers by Texas Instruments (Dallas, Tex.).

Amplifier 134 used to receive the signal from electrodes 116 is much simpler than the circuits found in conventional monitors. Because the device is body-worn and has no interconnecting lead wires or cables, the 60 Hz common mode rejection problems that challenge conventional monitors are nonexistent. Much of the dynamic range of conventional ECG circuits is occupied by the need to accept, and later filter out, low frequency phenomenon, such as the DC offset voltage present at the electrodes. However, the ECG signal in the present system 100 is used primarily for rate and rhythm analysis. The first operation performed in such analysis is often to severely high pass filter the ECG signal. For example, the rate-meter in many monitors utilizes an approximately 10 Hz high pass filter. If the amplifier is coupled to the ECG electrodes through capacitors, rather than directly, this high pass filtering can be performed before the signal even enters the amplifier. In this way, none of the dynamic range of the amplifier is wasted on DC offsets and other low-frequency artifacts. Therefore, a very modest circuit is used for amplifier 134. Further, this arrangement relieves the computing means 118 of the need to perform such filtering in software. Such a simplified amplifier can be constructed very compactly, using the highly miniaturized components available today. However, consideration is given to compatibility with patients having implanted pacemakers. Additional electronics and signal processing is required to identify and reject the pacemaker spikes, so that they do not interfere with the beat triggering.

In addition to the circuits shown in the block diagram, it is necessary to perform self-testing. In particular, the battery level must be monitored, the quality of the electrode contact verified, and all of the internal signal acquisition and processing functions checked. Analog to digital converter 136 embedded in computing means 118 has an input multiplexer (not shown) that allows it to also check the battery voltage. Computing means 118 can inject test currents into electrodes 116 to verify their impedance. Similarly, a test pulse can be injected into amplifier 134 to verify its gain. Various software checks can be used to verify the internal operation of computing means 118.

The average current consumption of each component is the product of its operating current and duty cycle. The following estimates assume a 3 Volt lithium battery as the power source. RF transmitter 120 consumes 5 µA on standby, and 12 mA when active. The average active current is therefore 12 mA times the 0.5% active duty cycle, or 60 µA. The average standby current is then 5 µA times the 99.5% standby duty cycle, or nearly 5 µA. Amplifier 134 operates on a 100% duty cycle, with 250 µA of current. Computing means 118, including internal analog to digital converter 136, consumes an average current of 600 µA. Patient identifier means 130 is disabled after it is initially interrogated, and therefore contributes nil to the average current consumption. The total average current consumption is the sum of these average figures, or 915 µA.

The power consumption estimate can be evaluated with respect to the capacities of some typical batteries. Inexpensive lithium coin cells are available with diameters in the range of 20 to 23 mm, and thicknesses varying from 1.6 to 3.2 mm, according to capacity. All of these cells cost under one dollar in quantity, with the least expensive being under 30 cents. Capacities range from 100 to 255 mA hours. Since the estimated current of the device is just under 1 mA, run times of 100 to 250 hours, or 4 to 10 days, are achievable with these inexpensive batteries.

The range of patient transmission means 114 is on the order of the size of a patient room or ward. Due to the short range of patient transmission means 114, receiving means must be placed at frequent intervals, such as in each room. The function of the receiving means R1-R4 is to collect the patient condition data from any patient transmission means 114 within its range. This data is then merged with an identifier of the receiving means location, and transmitted to central station means 112.

The manufacturers of RF transmitter 120 also produce complementary receiver modules which may be used in the receiving means. However, in the interests of achieving higher performance, it is desirable to use a somewhat more sophisticated receiver. In particular, it is desirable that the receiver include a means for quantifying the signal strength of the received patient condition data, as this is helpful in refining patient location when patient condition data is being received by more than one receiving means. In addition to considering signal strength, the phase or time of arrival of the received patient condition data at multiple receiving means can be used to refine the estimate of the transmission means location, by well-known triangulation means. Accordingly, it is preferred that the receiving means R1-R4 include a means for keeping track of the phase and/or time of arrival of the received patient condition data.

Once the patient condition data has been received and merged, it must be communicated to central station means 112. Since many receiving means may be connected to a single central station means 112, some type of networked link to central station means 112 is desirable. This could be a wired connection, such as an Ethernet. However, due to the large number of receiving means in some installations, the use of wired connections may be costly as a result of the expense of installing the wiring. In these cases, a second wireless link, from the receiving means to the central station means, is preferable. Wireless computer networking products are commercially available and therefore satisfactory technology is available off the shelf. These devices typically duplicate the functionality of a wired Ethernet via their wireless links. An example is a 2.4 GHz network operating with IEEE 802.11 protocol, available as a standard product from several manufacturers. Since the receiving means can be operated from the AC line, there are no special constraints regarding power consumption.

The wireless network products are available as small modules or cards that can be embedded into a product. In addition to means for communicating with central station means 112, the receiving means R1-R4 optionally may also contain a computing means, such as a microprocessor, which performs error checking of the received data, appends the identifier of the receiving means location and received signal strength indicator, and controls the communication of this merged data over the networked link to the central station. However, this too is a physically small device, allowing the entire receiving means to be made in a small enclosure self-supported by prongs that fit into an AC outlet, similar to common power adapter units. Therefore, installation is as simple as plugging the receiving means into an outlet in each room.

Central station means 112 receives the patient condition data from receiving means R1-R4, either by wire or wireless network. Central station means 112 may consist of custom software running on a PC, equipped with suitable commercial wired or wireless network connectivity. Central station means 112 performs a first task of sorting the received patient condition data, as data may have been acquired by more than one receiving means. The incoming data is then analyzed in two ways. The content of the data is analyzed for alarm conditions. High and low rate alarms could be provided at the central station means, although the detection of fatal arrhythmias is preferably performed in the transmission means. Second, the location of the receiving means receiving the strongest patient condition data signal strength is noted, providing the patient locator function. Associated with this is an evaluation of the patient condition data signal quality and monitoring of technical alarms, such as low battery, bad electrode, etc. Central station means 112 also contains the database that associates each patient's name with the numerical identifier obtained from the support serial number 133.

If desired, central station means 112 may further include a display for displaying the real time data for all patients, and may even log this to a patient trend database. Obviously, it is possible to sound a local alarm, and indicate the patient alarm condition and location on the unit's display. However, the system may be more valuable if it also directly notifies a response team. This can be done by an interface to a paging system 144 (FIG. 11). In the case of a paging system with alphanumeric capability, patient location can be transmitted. However, an interface to a voice pager or telephone system 146 (FIG. 11) is also possible using speech synthesis or voice messaging technology.

Note again that the present invention is not limited to use in monitoring patients in a hospital setting. Rather, the invention may be used to monitor conditions of any subject, including animate and inanimate objects, in a defined area. When monitoring the cardiac health of patients, the preferred embodiment uses an ECG waveform as a subject or patient signal; however, other signals indicative of the heart rate and rhythm can be used. The ECG is a convenient signal that may be acquired with high reliability and a minimum expenditure of power. Similar information, however, can be obtained from a plethysmographic signal. For example, a photoplethysmograph sensor could be arranged to operate in the reflectance mode, such that a plethysmographic signal is obtained from the tissue beneath the device. This signal would take the place of the ECG for rate and rhythm monitoring. In this case, the device need not be applied over the chest; it could be attached to any suitably perfused tissue. Alternatively, the device could be configured to use a more conventional transmission mode photoplethysmographic sensor, which could be applied to a suitable appendage such as the earlobe or finger. Similarly, the plethysmographic signal could be obtained by known impedance methods, such as by measuring the impedance of the tissue beneath the device by means of suitable electrodes.

Thus, it is understood that while particular examples have been described, it should be apparent to those skilled in the art that many modifications can be made without departing from the scope and intent of the invention. Accordingly, the invention is not limited to the specific embodiments thereof, except as defined in the appended claims.

I claim:

1. A monitoring device, comprising:
 a reusable portion comprising an electronic circuit, the electronic circuit comprising,
  a high pass filter,
  an amplifier,
  a processor configured to analyze analog sensor data to produce patient condition data, wherein the high pass filter is positioned before the amplifier and the amplifier is positioned before the processor in the electronic circuit, and wherein the processor is configured to identify a lethal arrhythmia, and
  a transmitter configured to transmit the patient condition data to a base station in real-time, wherein the patient condition data indicates occurrence of a lethal arrhythmia; and a disposable portion removably connectable to the reusable portion, the disposable portion comprising,
a power source, whereby power from the power source is supplied to the electronic circuit upon connection of the disposable portion to the reusable portion,
a physiological sensor connected to the disposable portion, whereby the physiological sensor is electrically connected to the electronic circuit when the disposable portion is connected to the reusable portion, and
an electronic identification tag associated with the disposable portion.

2. The monitoring device as claimed in claim 1, further comprising an adhesive support for adhering the monitoring device to a subject.

3. The monitoring device as claimed in claim 2, wherein the adhesive support is connected only to the disposable portion.

4. The monitoring device as claimed in claim 1, wherein the disposable portion further comprises a bar code label encoding a serial number matching the electronic identification tag.

5. A monitoring device, comprising:
a first portion including an electronic circuit, the electronic circuit comprising,
a high pass filter,
an amplifier,
a processor configured to analyze analog sensor data to produce patient condition data, wherein the high pass filter is positioned before the amplifier and the amplifier is positioned before the processor in the electronic circuit, and wherein the processor is configured to identify a lethal arrhythmia;
a disposable portion removably connectable to the first portion, the disposable portion comprising,
a power source, whereby power from the power source is supplied to the electronic circuit upon connection of the disposable portion to the first portion, and
an identification tag comprising an electronic identification tag and a barcode; and
an adhesive support for adhering the disposable portion to a subject.

6. The monitoring device as claimed in claim 5, further comprising:
a physiological sensor connected to the disposable portion, whereby the physiological sensor is electrically connected to the electronic circuit when the disposable portion is connected to the first portion.

7. The monitoring device as claimed in claim 5, wherein the electronic circuit includes a transmitter.

8. The monitoring device as claimed in claim 5, wherein the identification tag is operable to identify the subject.

9. The monitoring device as claimed in claim 5, wherein the barcode encodes an identifier matching the electronic identification tag.

* * * * *